US012727767B2

(12) United States Patent
Haase et al.

(10) Patent No.: US 12,727,767 B2
(45) Date of Patent: Sep. 8, 2026

(54) APPARATUS FOR DETERMINING A FUNCTIONAL INDEX FOR STENOSIS ASSESSMENT

(71) Applicant: KONINKLIJKE PHILIPS N.V., Eindhoven (NL)

(72) Inventors: Christian Haase, Hamburg (DE); Michael Grass, Buchholz in der Nordheide (NL); Bram Antonius Philomena Van Rens, Utrecht (NL); Roland Wilhelmus Maria Bullens, Mierlo (NL); Peter Maria Johannes Rongen, Eindhoven (NL); Arjen Van Der Horst, Tilburg (NL); Raoul Florent, Ville d'Avray (FR); Romane Isabelle Marie-Bernard Gauriau, Paris (FR); Javier Olivan Bescos, Eindhoven (NL); Holger Schmitt, Luetjensee (DE); Vincent Maurice André Auvray, Meudon (FR)

(73) Assignee: Koninklijke Philips N.V., Eindhoven (NL)

( * ) Notice: Subject to any disclaimer, the term of this patent is extended or adjusted under 35 U.S.C. 154(b) by 217 days.

(21) Appl. No.: 18/780,933

(22) Filed: Jul. 23, 2024

(65) Prior Publication Data

US 2024/0374148 A1 Nov. 14, 2024

Related U.S. Application Data

(63) Continuation of application No. 18/217,713, filed on Jul. 3, 2023, now Pat. No. 12,042,249, which is a (Continued)

(30) Foreign Application Priority Data

Sep. 30, 2016 (EP) .................................... 16191781

(51) Int. Cl.
*G06K 9/00* (2022.01)
*A61B 5/02* (2006.01)
(Continued)

(52) U.S. Cl.
CPC .......... *A61B 5/02007* (2013.01); *A61B 5/021* (2013.01); *A61B 5/026* (2013.01);
(Continued)

(58) Field of Classification Search
CPC ... A61B 5/0062; A61B 5/02007; A61B 5/021; A61B 5/026; A61B 5/1075;
(Continued)

(56) References Cited

U.S. PATENT DOCUMENTS 5,150,292 A * 9/1992 Hoffmann .............. A61B 6/507 600/431
9,757,073 B2 * 9/2017 Goshen .................. A61B 6/507
(Continued)

FOREIGN PATENT DOCUMENTS

WO 2012101584 A 8/2012
WO 2014072861 A2 5/2014
WO 2015059706 A2 4/2015

OTHER PUBLICATIONS

"Determination of Fractional Flow Reserve by Anatomic Computed Tomographic Angiography", https://clinicaltrials.gov/ct2/show/NCT01233518?term=DEFACTO&rank=1, Accessed Mar. 29, 2019.
(Continued)

*Primary Examiner* — Avinash Yentrapati

(57) ABSTRACT

An apparatus for determining a functional index for stenosis assessment of a vessel is provided. The apparatus comprises an input interface (40) and a processing unit (50). The input interface is configured to obtain image data (30) representing a two-dimensional representation of a vessel (6). The processing unit (50) is configured to determine a course of
(Continued)

the vessel (6) and a width (w1, w2) of the vessel along its course in the image data and is further configured to determine the functional index for stenosis assessment of the vessel based on the width of the vessel in the image data.

11 Claims, 2 Drawing Sheets

Related U.S. Application Data continuation of application No. 17/531,899, filed on Nov. 22, 2021, now Pat. No. 11,690,518, which is a continuation of application No. 16/338,290, filed as application No. PCT/EP2017/075021 on Oct. 2, 2017, now Pat. No. 11,179,043.

(51) Int. Cl.
*A61B 5/021* (2006.01)
*A61B 5/026* (2006.01)
*A61B 5/107* (2006.01)
*A61B 6/00* (2006.01)
*G06T 7/62* (2017.01)

(52) U.S. Cl.
CPC .......... *A61B 5/1075* (2013.01); *A61B 6/5217* (2013.01); *G06T 7/62* (2017.01); *A61B 5/1079* (2013.01); *G06T 2207/10116* (2013.01); *G06T 2207/30104* (2013.01)

(58) Field of Classification Search
CPC ..... A61B 5/1076; A61B 5/1079; A61B 6/481; A61B 6/504; A61B 6/5217; G06T 2207/10116; G06T 2207/30101; G06T 2207/30104; G06T 7/62
See application file for complete search history.

(56) References Cited

U.S. PATENT DOCUMENTS 10,111,633 B2* 10/2018 Nickisch ................ A61B 6/463
10,622,110 B2 4/2020 Itu
10,646,185 B2* 5/2020 Goshen .................. G16H 30/20
2007/0053558 A1 3/2007 Puts
2011/0071404 A1 3/2011 Schmitt
2014/0200867 A1 7/2014 Lavi
2014/0236011 A1* 8/2014 Fan ...................... A61B 8/4477 600/407
2015/0051888 A1* 2/2015 Itu .......................... G16H 50/50 703/2
2015/0265162 A1* 9/2015 Lavi ....................... A61B 6/504 600/408
2015/0268039 A1 9/2015 Tu
2015/0282765 A1* 10/2015 Goshen .................. A61B 6/504 600/408
2015/0339847 A1* 11/2015 Benishti ................. A61B 6/466 382/131
2015/0342551 A1* 12/2015 Lavi ....................... G16H 50/50 600/407
2015/0356753 A1 12/2015 Lauritsch
2016/0073970 A1 3/2016 Sharma
2016/0247279 A1* 8/2016 Lavi ...................... G06T 7/0014
2016/0302750 A1* 10/2016 Nickisch ............. A61B 6/5217
2017/0095221 A1* 4/2017 Kato ...................... G16H 30/40
2017/0105694 A1* 4/2017 Grass ....................... A61B 6/06
2018/0032653 A1* 2/2018 Aben ...................... G06F 30/20
2020/0251223 A1* 8/2020 Lavi ....................... G16H 50/30

OTHER PUBLICATIONS

"FAME II—Fractional Flow Reserve (FFR) Guided Percutaneous Coronary Intervention (PCI) Plus Optimal Medical Treatment (OMT) Verses OMT", https://clinicaltrials.gov/ct2/show/NCT01132495?cond=FAME&rank=6, Accessed Mar. 29, 2019.
Morris et al., "Virtual Fractional Flow Reserve From Coronary Angiography: Modeling the Significance of Coronary Lesions" JACC: Cardiovascular Interventions, Journal of the American College of Cardiology, 2013, 6, 149-157.
Papafaklis, M. et al., "Fast virtual functional assessment of intermediate coronary lesions using routine angiographic data and blood flow simulation in humans: comparison with pressure wire—fractional flow reserve", EuroIntervention, https://www.pcronline.com/eurointervention/76th_issue/volume-10/number-5/100/fast-virtual-functional-assessment-of-intermediate-coronary-lesions-using-routine-angiographic-data-and-blood-flow-simulation-in-humans-comparison-with-pressure-wire-fractional-flow-reserve.html, Jul. 2014.
Gökgöl, Can, et al. "Quantification of popliteal artery deformation during leg flexion in subjects with peripheral artery disease: a pilot study." Journal of Endovascular Therapy 20.6 (2013): 828-835.
Ghriallais, Ríona Ní, and Mark Bruzzi. "Effects of knee flexion on the femoropopliteal artery: A computational study." Medical engineering & physics35.11 (2013): 1620-1628.

* cited by examiner

APPARATUS FOR DETERMINING A FUNCTIONAL INDEX FOR STENOSIS ASSESSMENT

CROSS-REFERENCE TO PRIOR APPLICATIONS

This application is a continuation of U.S. application Ser. No. 18/217,713, filed on 3 Jul. 2023, now U.S. Pat. No. 12,042,249, which is a continuation of U.S. application Ser. No. 17/531,899, filed on 22 Nov. 2021, now U.S. Pat. No. 11,690,518, which is a continuation of U.S. application Ser. No. 16/338,290, filed on 29 Mar. 2019, now U.S. Pat. No. 11,179,043, which is the U.S. National Phase application under 35 U.S.C. § 371 of International Application No. PCT/EP2017/075021, filed on 2 Oct. 2017, which claims the benefit of European Patent Application No. 16191781.0, filed on 30 Sep. 2016. These applications are hereby incorporated by reference herein.

FIELD OF THE INVENTION

The present invention relates to an apparatus for determining a functional index for stenosis assessment of a vessel, a method for determining a functional index for stenosis assessment of a vessel, a related computer program product and a computer-readable medium having stored said computer program product.

BACKGROUND OF THE INVENTION

Cardiovascular diseases are a leading cause of death in the industrialized world. The predominant form of cardiovascular disease results from the chronic build-up of a fatty material ("plaque") in the inner tissue layer of the arteries supplying the heart, brain, kidneys and lower extremities. Such build-up of plaque in the arteries may lead to a narrowing of the lumen of the vessel, which narrowing is referred to as a stenosis.

Progressive coronary artery disease such as vessel stenosis restricts blood flow to the heart. Assessing a blood flow through a vessel may require various examination procedures, be it invasive or non-invasive ones. Due to the lack of accurate information provided by current non-invasive tests, many patients require invasive catheter procedures to assess a blood flow through a vessel.

Recent studies have demonstrated that hemodynamic characteristics, such as fractional flow reserve (FFR), may be important indicators to assist in determining optimal treatment for a patient with arterial disease. Some of the conventional assessments of the fractional flow reserve use invasive catheterization to directly measure blood flow characteristics, such as pressure and flow velocities. However, these invasive measurement techniques present a risk to the patient and may result in significant costs.

FFR is an index of the functional severity of a stenosis that is calculated from pressure measurements, preferably made during arteriography. The FFR may be defined as the distal blood pressure (behind a stenosis or downstream of it when viewed in flow direction of the blood) relative to the proximal pressure (behind the stenosis or upstream of it when viewed in flow direction of the blood) under hyperemic conditions (i.e. the ratio between the pressure after a lesion and the normal pressure). In other words, the fractional flow reserve expresses the maximum flow down a vessel, in particular in the presence of a stenosis compared to the maximal flow in the hypothetical absence of the stenosis. The fractional flow reserve is a normalized value in the range between 0 and 1, wherein the fractional flow reserve of 0.5 indicates that a given stenosis causes a 50% drop in blood pressure and thus restricts the maximum blood flow capacity in the vessel significantly.

Alternatively, the Instantaneous Free-Wave Ratio (iFR) may be used as an indicator for the remaining flow maximum flow capacity.

However, the amount of effort required for stenosis assessment may be very high and may require a lot of information, in particular for non-invasive stenosis assessment.

WO 2014/072861 A2 describes determination of a fractional flow reserve based on certain extracted features. The features are extracted from a volumetric representation of a region of interest of a patient's body. Furthermore, boundary conditions for determining an FFR via simulation are determined and these boundary conditions can be used to classify the unknown FFR.

SUMMARY OF THE INVENTION

In view of the above, there may be a need to reduce the effort required for stenosis assessment and to simplify the process therefor.

This need is fulfilled by the subject-matter of the independent claims, wherein further embodiments are incorporated in the dependent claims. It should be noted that the following described aspects of the invention apply also for the method, the computer program element and the computer-readable medium, at least in an analogous manner.

According to a first aspect of the invention, an apparatus for determining a functional index for stenosis assessment of a vessel is provided. The apparatus comprises an input interface and a processing unit. The input interface is configured to obtain image data representing a two-dimensional representation of a vessel. The processing unit is configured to determine a course of the vessel and a width of the vessel along its course in the image data and is further configured to determine the functional index for stenosis assessment of the vessel based on the width of the vessel in the image data.

The input interface may receive image data in any data format, wherein the image data correspond to a two-dimensional representation of a region of interest of a patient's body. The image data may be captured by various possible image capturing devices as long as the image data are a two-dimensional representation of a region of interest containing at least one vessel, in particular at least one blood vessel. In other words, the input interface is adapted to receive two-dimensional (2D) image data. The input interface may be an optical capturing unit which is adapted to scan an image. The processing unit may be adapted to process the scanned image data and to identify a blood vessel as well as to determine the functional index for stenosis assessment based on the width of the blood vessel. The width may be, in particular, an internal width of the vessel such that the width identifies the space or diameter available for the blood flow. Alternatively, the input interface may be adapted to receive data representing a two-dimensional image, which data are provided by an external unit.

The image data may be provided by an X-ray imaging system, wherein the vessel or vessels in a region of interest are projected onto a two-dimensional image plane while the blood flowing through the vessel(s) contain a contrast agent such that the internal diameter of the vessel is represented in the image. Thus, the 2D image data is acquired using X-ray angiography. In particular, angiography images of the coronary arteries of the patient may be acquired.

The functional index for stenosis assessment may be, for example, a fractional flow reserve indicator. However, other indicators, such as the above mentioned iFR, may be possible, as well.

According to a further aspect of the invention, a method for determining a functional index for stenosis assessment is provided, wherein the method comprises the following steps:

a) obtaining image data corresponding to two-dimensional image data of a vessel;

b) determining a course of the vessel and a width of the vessel along its course in the image data;

c) determining a functional index for stenosis assessment of the vessel based on the width of the vessel in the image data.

For example, the two-dimensional image data may be a projection of a spatial object, e.g., a body having at least one vessel, onto a two-dimensional surface resulting in a two-dimensional image of the at least one vessel.

The approach described herein and the findings the approach is based on may be summed up as follows:

Quantitative assessment of stenosis in the human arteries is highly desirable for interventional decision making. Current concepts typically include purely geometric assessment of stenosis diameter, length, cross-sectional area and derived quantities. These can be determined from a single 2D angiographic projection (2D QCA, quantitative coronary angiography) or from multiple 2D projections or rotational sequences (3D QCA).

Recently, a shift from geometric stenosis assessment towards functional assessment is happening. Functional measures also consider the impact of the stenosis on blood flow. Specifically, virtual Fractional Flow Reserve (vFFR) aims to predict measured fractional flow reserve (FFR). Virtual FFR can be calculated by applying computational fluid dynamics (CFD) to a 3D vessel geometry model from CT image volumes or 3D angiographic datasets.

For workflow simplicity, it would be highly desirable to generate a functional index using a single 2D projection image.

This is done in accordance with the apparatus and the method described above substantially as follows:

determining a geometric model of at least a section of a vessel, the model including an inner diameter and a change of the diameter along the course of the vessel;

determining at least one resistance value of at least the section of the vessel based on the geometric model;

determining a pressure drop of a fluid which flows through said vessel or section of the vessel based on the at least one resistance value.

The determined pressure drop is an equivalent of the functional index for stenosis assessment.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

In the following, the invention is exemplarily described as being used in the context of the apparatus for determining a functional index for stenosis assessment. However, the invention can also be used in the context of the method for determining a functional index for stenosis assessment. Thus, all the following examples and/or explanations may also be intended as being implemented by the method of the invention. Features relating to the apparatus are to be understood as to similarly apply to the method, as well, and vice versa.

Figure 1:
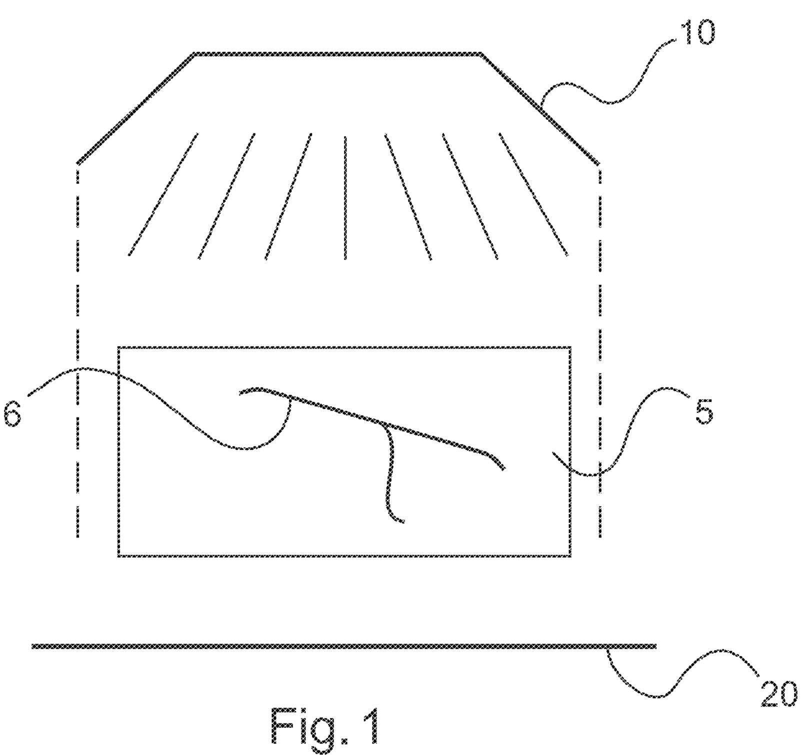
FIG. 1 schematically illustrates an imaging system.

FIG. 1 schematically illustrates an imaging system 10, for example an X-ray system, for generating image data of a region of interest of an object 5, for example of a part of the human body. The imaging system 10 may emit X-ray radiation towards and through the object such that the composition of the object is projected onto the projection surface 20. Thus, a two-dimensional image is generated which can be used as input data for the apparatus described herein.

However, it should be noted that image data generated by other means or by other processes may be used as input data for the apparatus as long as the image data are a two-dimensional representation of a spatial object like the human body.

Figure 2:
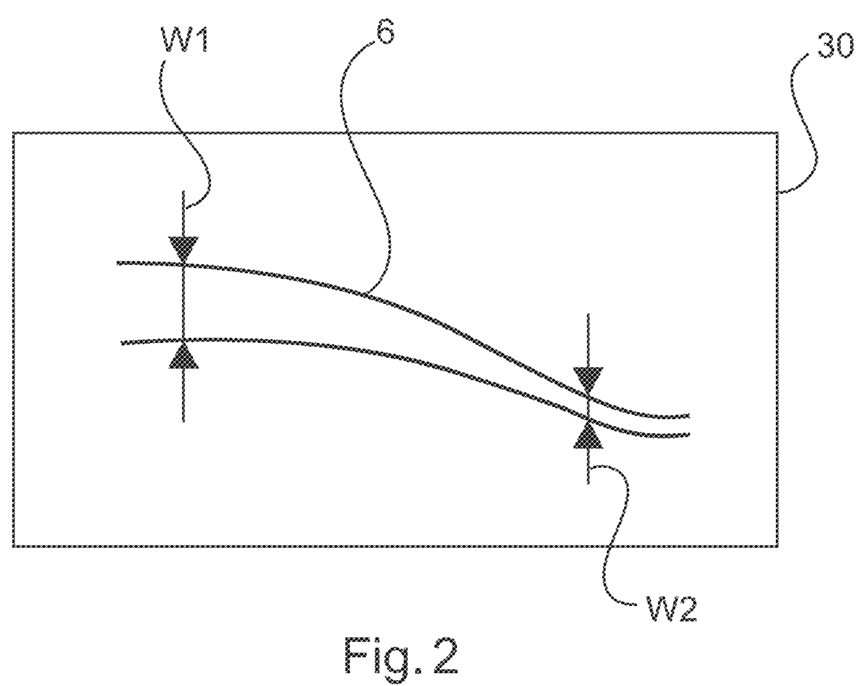
FIG. 2 schematically illustrates two-dimensional image data for being used by an apparatus according to an exemplary embodiment.

FIG. 2 schematically shows an image 30 containing a projection of a section of a vessel 6 in a two-dimensional projection. In this two-dimensional image, the section of the vessel 6 does not have a constant diameter but the diameter changes. In particular, the diameter W1 at the left side is greater than the diameter W2 at the right side of the image 30.

The functional index for stenosis assessment for the shown section of vessel 6 is determined as follows:

determining a geometric model of at least a section of a vessel, the model including an inner diameter of a vessel or a section of the vessel and the change of the diameter along the course of the vessel. This may be done, for example, by partitioning the section of vessel 6 as to have multiple partitions and determining a diameter or mean diameter for each partition; the higher the numbers of partitions, the more exact may be the functional index for stenosis assessment;

determine at least one resistance value of at least the section of the vessel based on the geometric model. With reference to FIG. 2, a simulated fluid flowing from the left to the right would experience an increasing fluid dynamic resistance if W2 is smaller than W1, for example due to a stenosis. In particular, the vessel or vessel segment may be approximated by at least one linear or non-linear resistor, preferably a series of such resistors.

determine a pressure drop of a fluid which flows through said vessel or section of the vessel based on the at least one resistance value. For example, the pressure drop may be determined using a lumped element fluid dynamics model, including the determined resistance value or values and certain boundary conditions. For example, assumptions may be made regarding the (volumetric) flow rate and/or pressure at the inlet and/or outlet of the vessel or vessel section, which assumptions are then used as boundary conditions in the lumped elements model. Alternatively, physical measurement values, such as an aortic pressure measurement, may be used as boundary conditions.

The determined pressure drop, for example over a stenosis in a coronary vessel segment, is an equivalent of the functional index for stenosis assessment.

Figure 3:
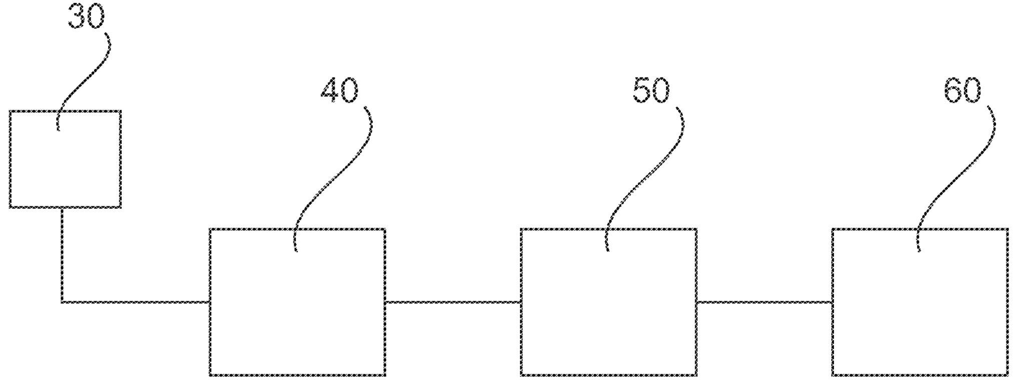
FIG. 3 schematically illustrates an apparatus according to an exemplary embodiment.

FIG. 3 shows an apparatus for determining a functional index for stenosis assessment. The apparatus comprises an interface 40 for receiving image data representing a two-dimensional image, a processing unit 50, and an output unit 60. Even though the output unit 60 is shown in FIG. 3, this is not a necessarily required component of the apparatus. The processing unit may determine the functional index for stenosis assessment and may store this value in a memory unit or storage unit such that an external output unit may access said memory unit or storage unit to read out the functional index for stenosis assessment.

The interface 40 is configured for receiving image data 30. The image data may be provided as pictures or projections of body regions or as digital data transmitted to the interface 40 via a suitable data transmission protocol either via a data transmission network or by accessing kind of memory unit which stores the image data.

The output unit may be a device for optically indicating the functional index for stenosis assessment. For example, the output unit may be a monitor or any other kind of display.

According to an aspect of the invention, the input interface is configured to obtain image data representing a two-dimensional representation of a vessel and the processing unit is configured to determine a course of the vessel and a width of the vessel along its course in the image data and is further configured to determine the functional index for stenosis assessment of the vessel based on the width of the vessel in the image data.

The input interface may receive image data in any format. The input interface is adapted to receive two-dimensional image data, in particular. Especially, only a single two-dimensional representation (a projection, for example) of a vessel is used for determining the functional index for stenosis assessment, for example a fractional flow reserve.

According to an embodiment, the two-dimensional image data of the vessel represents a two-dimensional image of a blood vessel of a human.

According to an embodiment, the two-dimensional image is a projection of the vessel.

According to an embodiment, the width of the vessel corresponds to a diameter of the vessel in an image plane or projection plane.

As an effect, coronary lesion hemodynamic significance may be estimated based on fractional flow reserve, for example.

According to an embodiment, the processing unit is configured to apply a densitometry method to the image data as to compensate for foreshortening effects in the image data when determining the width of the vessel.

Densitometry is used for quantitative measurement of optical density. By means of the densitometry method, it may be determined if the distance of the vessel from the image plane or projection plane varies along the course of the vessel and this may be additionally considered when determining the width of the vessel. This may be done as to not adulterate the determined width value of the vessel as a result of the varying distance from the image plane or projection plane. In other words, the measured width may be corrected based on the results of the densitometry method.

The densitometry may be used to compensate for foreshortening in the projection/two-dimensional image and the width may be determined based on both the diameter in the projection and the result of the densitometry measurement by accumulating the results of these approaches.

According to an embodiment, the processing unit is configured to apply a scaling factor to the width of the vessel in the image and to determine the functional index for stenosis assessment based on the width multiplied by the scaling factor.

Thus, a non-magnified size of the vessel may be determined and the functional index for stenosis assessment is determined based on this corrected vessel diameter.

According to an embodiment, the processing unit is configured to receive the distance of the projected vessel from a projection plane of the projected image data and to determine the scaling factor based on said distance.

The magnification of the vessel width in the image or projection is dependent on the distance of the vessel from the image or projection surface, respectively. This distance may be considered when determining the scaling factor to get a more accurate result.

According to an embodiment, the processing unit is configured to segment the vessel along its course such that there are multiple vessel segments or partitions and to apply a specific scaling factor to the width of each one of the multiple vessel segments or partitions.

As a projection of the vessel or a two-dimensional image of the vessel are used, the width along the course of the vessel in the projection or image may not be true to scale. Therefore, it may be necessary to apply different scaling factors to the width of the segments of the vessel in order to determine the non-magnified width.

According to an embodiment, the processing unit is configured to segment the vessel such that one segment of the vessel has substantially the same distance from the projection surface.

Thus, there is an appropriate segmentation such that there is almost the same magnification of the diameter within one segment and it may be ensured that the scaling factor is applicable to the entire segment without artificially adding distortion or bias to the width of the vessel.

The segmentation may be done such that the distance of the vessel within one segment is within a corridor of a predetermined width around the medium distance of the segment, for example within 5% or 10% around the medium distance.

According to an embodiment, the processing unit is configured to detect a reference element within the image data and to determine the scaling factor based on a known size of the reference element and the size of the reference element in the image data.

Thus, the scaling factor of the vessel may be determined based on the known dimensions of the reference element in a more accurate manner.

According to an embodiment, the processing unit is configured to determine a functional index for stenosis assessment based on the width of the vessel in the image data, wherein the functional index is one of: a pressure drop along a centreline of the vessel, a virtual fractional flow reserve, a curve of the pressure drop as a function of the blood flow through the vessel, a fluid-dynamic resistance value, a blood velocity profile, a blood velocity distribution.

In general, any parameter or any functional index that can be derived from hemodynamic parameters (e.g. coronary flow reserve, CFR, instant flow reserve, iFR) may be used individually or in combination with any one or multiple of the abovementioned indicators.

According to an embodiment, the vessel is an artery of a human body.

Figure 4:
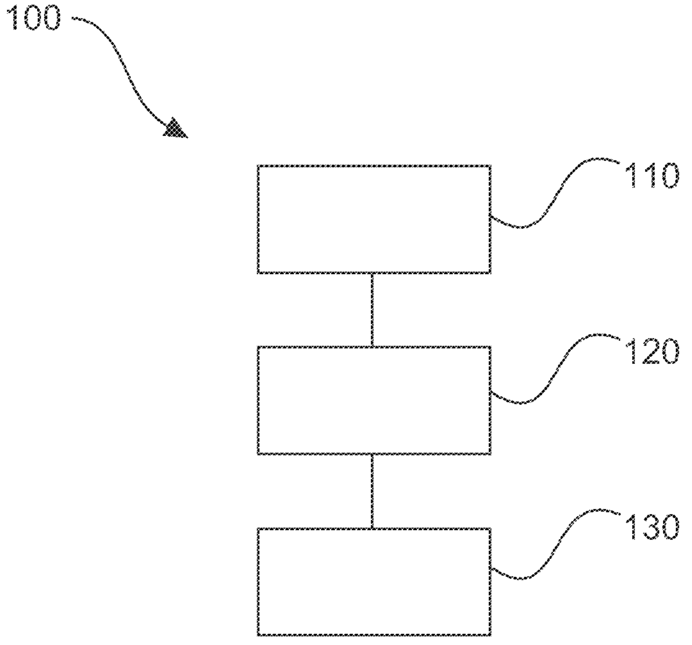
FIG. 4 schematically illustrates a flow chart of a method according to an exemplary embodiment.

FIG. 4 schematically illustrates a flow chart 100 of a method for determining a functional index for stenosis assessment. The method comprises the following steps:

In a first step 110, also referred to as step a), image data corresponding to two-dimensional image data of a vessel are obtained.

In a second step 120, also referred to as step b), a course of the vessel and a width of the vessel along its course in the image data is determined.

In a third step 130, also referred to as step c), a functional index for stenosis assessment of the vessel is determined based on the width of the vessel in the image data. It is understood that, without repeating here all the explanations, examples, features and/or advantages provided with reference to the apparatus for determining a functional index for stenosis assessment, the method of the invention is intended to be configured to carry out the method steps 110 to 130 for which the apparatus is configured to. Thus, all the above examples, explanations, features and/or advantages, although provided previously with reference to the apparatus for determining a functional index for stenosis assessment, are also intended to apply in a similar manner to the method and to, in particular for the following exemplary embodiments of the method.

According to an exemplary embodiment of the method, the step of obtaining image data comprises obtaining a projection of the vessel, wherein the width of the vessel is determined based on the projection.

According to an exemplary embodiment, the method further comprises the steps of: determining a length of the vessel in the image; determining a scaling factor based on a densitometry approach; applying the scaling factor to the determined width of the vessel.

According to a further example of the present invention, a computer program element is provided, which, when being executed by a processing unit is adapted to carry out the method described above.

According to further example of the present invention, a computer readable medium having stored thereon a program element is provided, which, when being executed by a processing unit is adapted to carry out the method described above.

In other words, the approach described above relating to the apparatus and method for determining a functional index for stenosis assessment may be summed up as follows and it is proposed here to approximate this by one or more of the following:

Apply 2D QCA methods to obtain a 2D segmentation and a vessel centerline of the culprit vessel segments. In order to estimate the non-magnified size of the vessel diameter and length, the scaling factor due to magnification can be estimated from either of the known system geometry and an estimate of the position of the heart inside the X-ray system, the known size of the catheter at the ostium of the contrary artery tree, or a phantom/reference element placed on the chest wall of the patient.

Thus, a geometric model including a centerline and the local vessel radius $r_i$ for each centerline point are determined. This may include branching points.

The geometric model further includes cross-sectional areas that are estimated for one or more of the centerline points. For example, such estimate is made for each centerline point. In a first approximation, this is $A_i=\pi*r_i^2$.

Thus, a simple geometric model of the segmented vessel is generated, which is used as a basis for a subsequent calculation of a functional index.

In one embodiment, densitometric information is used to estimate the vessel diameter in the through-plane direction. This may be based on cardiac digital subtraction angiography (DSA). Furthermore, this may utilize a time series images over a complete cardiac cycle to improve the robustness of the densitometric measurement. Densitometric evaluation might be limited to a segment of the vessel, e.g. between two bifurcations.

In another embodiment, the projection angle is chosen such that the apparent stenosis diameter is minimized. This choice may be done manually by a human operator of an imaging system by selecting one of multiple acquired projections, or an automatic suggestion is made based on prior-knowledge using a reference database of projection images. This approach may result in a systematic underestimation of the cross-sectional area, and may lead to improved reproducibility as compared to an unguided approach.

In another embodiment, the projection angle is chosen (manually or automated) such that least vessel foreshortening occurs. This may be combined with the diameter minimization.

Based on some or all of the vessel characteristics that are extracted from 2D images (like diameter, length, curvature, through plane diameter, bifurcation number and location), a functional index for stenosis assessment is calculated. This functional index can, for instance, be either of: the pressure drop along the centerline of the vessel, virtual FFR, e.g. based on CFD simulations, a curve of the pressure drop as a function of the blood flow through the stenosis, or a quantity derived thereof, a fluid-dynamic resistance value, simulated average blood velocity profile or velocity distribution, or any other functional index that can be derived from hemodynamic parameters (e.g. CFR, iFR, etc.).

In an embodiment, the functional index for stenosis assessment is derived from a 2D projection image. Preferably, a single angiographic 2D projection image with segmentation and pressure drop profile is used for functional assessment, as it can be obtained from fluid dynamics simulations.

However, additionally, the index may be independently derived from a plurality of 2D images. That is, a functional index being derived "independently" involves deriving separate indices for individual images in a series, for instance carrying out the vessel segmentation, modeling and fluid dynamics simulation for each image of the series.

Different images in the series are for example acquired in different cardiac states. Alternatively or in addition, different projection angles may be used providing different viewing angles on the vasculature.

Optionally, an improved assessment can be based on one or more of the functional indices derived from different images. For example, in this case, it may be helpful to merge the individual numbers into a combined index (e.g. the mean value).

Alternatively or in addition, a variation between the functional indices from different images is determined. For example, such variation can be compared to a predetermined maximal variation (Vmax), based on which an acceptance criterion may be generated, in order to have feedback on the accuracy of the results. If the simulated values from multiple images are within expected or predetermined limits of variation, the acceptance criterion may indicate that the simulated results may be accepted with higher confidence than for a single frame evaluation.

The expected maximal variation (Vmax) may be predetermined taking into account the nature of the different images of the sequence. For example, for multiple images taken at the same projection angle but in different heart phases, Vmax may be lower than for multiple images taken at different projection angles.

Alternatively or in addition, the processing unit may be configured to calculate a quality score for one or more images being used as a basis for calculating the functional index for stenosis assessment.

For example, such quality score may be based on one or more of the following quality parameters:

The resolution of the angiographic X-ray image, as may for example be determined from DICOM data associated with the image.

The size of the projected vessel tree, e.g. an image area covered by contrast-enhanced vessels. A larger projected vascular tree may represent a higher quality image.

The amount of noise in the projection, as may for example be determined by means of a noise measurement in a background area, i.e. a portion of the image outside the vascular tree. A lower amount of noise may represent a higher quality image.

A sharpness of projection, as may for example be determined by means of an entropy analysis or gradient measures.

The motion of the coronary arteries, as may for example be determined by means of a correspondence analysis with neighbouring images in a sequence. Strong motion may lead to blurred contours and thereby a lower quality image.

Other quality parameters, such as the amount of foreshortening in the projection image for the section of vessel of interest, or the amount of vessel overlap in the projection image, could also be taken into consideration.

In an embodiment, the quality score may be visualized together with the angiographic X-ray image, the calculated functional index and, optionally, the determined segmentation of the vessel segment of interest.

In a further embodiment, if the functional index is independently derived for a plurality of images, the quality score may be calculated for each image together with the functional index. For example, the quality score may then be used as a weighting factor in determining a combined functional index, whereby a functional index derived from a lower quality image is given less weight in the combined index as a functional index derived from a higher quality image.

The approach described herein is applicable for functional assessment of stenosis in all major arteries of the human body (coronaries, iliac, femoral, brachial, hepatic, carotids).

In an embodiment, the functional index may be compared to one or more geometric measures for example obtained by means of QCA. Automatic QCA measurements may be carried out along the centerline of the vessel or vessel section of interest. Likewise, an FFR value may be calculated for the same vessel or vessel section.

For example, a user interface may be provided that enables such comparison. Both the QCA and FFR values can be normalized and overlaid on top of the angiographic X-ray image that was used as a basis for the calculations. In an example, portions of the vessel where a discrepancy between the normalized QCA and FFR values exceeds a predetermined threshold may be determined and visualized on the image, for instance by means of highlighting or color coding. The normalization may be based on standard decision thresholds, e.g. a threshold for a decision whether a stent is to be placed or not. In that case, a QCA value of 0.5 may correspond to an FFR value of 0.8.

It has to be noted that embodiments of the invention are described with reference to different subject matters. In particular, some embodiments are described with reference to a method whereas other embodiments are described with reference to the apparatus. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features. While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single parameter, feature or other element may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method, comprising:

determining a geometric model of a vessel comprising a stenosis, wherein the geometric model comprises an inner diameter and a change of the inner diameter along a course of the vessel, wherein the change of the inner diameter is representative of the stenosis;

determining a resistance value of the vessel based on the geometric model;

determining a functional index for stenosis assessment corresponding to a flow of a fluid through the vessel, wherein the functional index for stenosis assessment is equivalent to a pressure drop of the fluid across the stenosis, wherein the functional index for stenosis assessment is determined based on:

the resistance value; and a boundary condition comprising at least one of:

a volumetric flow rate associated with an inlet of the vessel;

the volumetric flow rate associated with an outlet of the vessel;

a pressure associated with the inlet; or the pressure associated with the outlet; and outputting, on a display, an indication of the functional index for stenosis assessment, wherein the functional index for stenosis assessment is distinct from the inner diameter and the change of the inner diameter.

2. The method of claim 1, further comprising:

determining a width of the vessel; and applying a scaling factor to the width, wherein the determining the functional index for stenosis assessment is based on the width multiplied by the scaling factor.

3. The method of claim 2, wherein determining the width of the vessel comprises applying a densitometry method.

4. The method of claim 2, further comprising:

receiving a distance of the vessel from an image plane; and determining the scaling factor based on the distance.

5. The method of claim 2, further comprising:

segmenting the vessel along the course of the vessel such that there are multiple vessel segments; and applying a specific scaling factor to the width of each one of the multiple vessel segments.

6. The method of claim 5, wherein the segmenting the vessel is based on a distance between a vessel segment and a projection surface.

7. The method of claim 2, further comprising:

detecting a reference element within image data; and determining the scaling factor based on a known size of the reference element and the known size of the reference element in the image data.

8. The method of claim 1, further comprising:

independently deriving a plurality of functional indices for stenosis assessment.

9. The method of claim 8, further comprising:

determining a variation between the plurality of functional indices for stenosis assessment;

comparing the variation to a predetermined maximal variation; and generating an acceptance criterion based on the comparing.

10. The method of claim 1, wherein the determining the functional index for stenosis assessment uses a lumped element fluid dynamics model including the resistance value and the boundary condition.

11. A non-transitory computer-readable medium having stored thereon a computer program for:

determining a geometric model of a vessel comprising a stenosis, wherein the geometric model comprises an inner diameter and a change of the inner diameter along a course of the vessel, wherein the change of the inner diameter is representative of the stenosis;

determining a resistance value of the vessel based on the geometric model;

determining a functional index for stenosis assessment corresponding to a flow of a fluid through the vessel, wherein the functional index for stenosis assessment is equivalent to a pressure drop of the fluid across the stenosis, wherein the functional index for stenosis assessment is determined based on:

the resistance value; and a boundary condition comprising at least one of:

a volumetric flow rate associated with an inlet of the vessel;

the volumetric flow rate associated with an outlet of the vessel;

a pressure associated with the inlet; or the pressure associated with the outlet; and outputting, on a display, an indication of the functional index for stenosis assessment, wherein the functional index for stenosis assessment is distinct from the inner diameter and the change of the inner diameter.

* * * * *